United States Patent [19]

Coutel-Egros

[11] Patent Number: 5,244,881
[45] Date of Patent: Sep. 14, 1993

[54] COMPOSITIONS BASED ON IMIPYRAMINE

[75] Inventor: Anne Coutel-Egros, Palaiseau, France

[73] Assignee: Rhone-Poulenc Sante, France

[21] Appl. No.: 776,344

[22] PCT Filed: May 22, 1990

[86] PCT No.: PCT/FR90/00359
§ 371 Date: Nov. 22, 1991
§ 102(e) Date: Nov. 22, 1991

[87] PCT Pub. No.: WO90/14089
PCT Pub. Date: Nov. 29, 1990

[30] Foreign Application Priority Data

May 24, 1989 [FR] France .................. 89/06781

[51] Int. Cl.$^5$ ............... A61K 31/645; A61K 9/18; A61K 47/48
[52] U.S. Cl. .................... 514/58; 536/103; 540/587; 540/595
[58] Field of Search ............ 514/58; 536/103; 540/587, 595

[56] References Cited

U.S. PATENT DOCUMENTS

| | | | |
|---|---|---|---|
| 4,165,382 | 8/1979 | Pozuelo | 514/567 |
| 4,284,555 | 8/1981 | Gold et al. | 540/595 |
| 4,349,472 | 9/1982 | Gold et al. | 540/595 |
| 4,477,378 | 10/1984 | Gold et al. | 540/595 |
| 4,758,566 | 7/1988 | Uno et al. | 514/254 |

FOREIGN PATENT DOCUMENTS 251459 1/1988 European Pat. Off.

OTHER PUBLICATIONS

Chemical Abstracts, vol. 108, No. 14, 108:118829d, Apr. 4, 1988.
Chemical Abstracts, vol. 111, No. 21, 111:194557r, Nov. 20, 1989.
Chem. Pharm. Bull., vol. 23, No. 12 (1975), pp. 3062-3068.

Primary Examiner—Ronald W. Griffin
Attorney, Agent, or Firm—Morgan & Finnegan

[57] ABSTRACT

The invention provides new inclusion compounds based on imipramine and cyclodextrin and pharmaceutical compositions which can be administered orally and are based on these new inclusion compounds.

4 Claims, No Drawings

COMPOSITIONS BASED ON IMIPYRAMINE

The present invention relates to compositions based on imipramine or one of its derivatives, and more particularly to pharmaceutical compositions for oral administration of imipramine or one of its derivatives.

Imipramine is currently marketed under the trade name Tofranil in the form of tablets or of a solution based on the hydrochloride. Trimipramine, which is a derivative of imipramine, is marketed under the trade name Surmontil in the form of tablets or a solution; the tablets consist of trimipramine maleate, while the solutions are made up of methanesulphonate.

The aqueous solutions of imipramine or trimipramine have two disadvantages: on the one hand, they are very bitter, which makes their oral administration not readily acceptable, especially for children and elderly people, and on the other hand the division of aqueous forms is always a problem, in outpatient treatment, especially for elderly people. These solutions also display a surprising phenomenon; when they are evaporated to dryness the product obtained, which initially is crystalline, is in the form of a gum which it is impossible to redissolve and which no longer permits preparation in any pharmaceutical form. The nature of the conversion product after dissolving in aqueous solution is unknown to date.

The present invention resolves the two above mentioned disadvantages, that is to say the bitterness of the aqueous solutions and the formation of gum, which are not interrelated in any way, by means of a single solution. This solution consists in enclosing imipramine or its derivatives and its salts in cyclodextrin.

This enclosure requires at least two, preferably between two and fifteen, moles of cyclodextrin per mole of imipramine, or of a derivative or salt thereof.

Amongst the derivatives of imipramine, trimipramine may be mentioned, and amongst its salts, the hydrochloride and the methanesulphonate may be mentioned. The cyclodextrin used is chosen from α-cyclodextrin, β-cyclodextrin and γ-cyclodextrin. It is preferred to use β-cyclodextrin.

The process for enclosing imipramine or its derivatives and its salts in cyclodextrin consists in dissolving imipramine, its derivative or its salt and cyclodextrin in a small amount of water or solvent, carefully mixing the mixture obtained and evaporating the said mixture. This evaporation can be carried out equally well by lyophilisation, without the need to add either a diluent or a binder, or by drying by any means, such as, for example, an oven.

The pulverulent inclusion compound obtained after evaporation can be brought into a pharmaceutical form, such as filled into sachets, or made into tablets or granules. It is always possible, before the composition is brought into its final form, to add sweeteners, flavourings, sugaring agents, preservatives and colorants. Within the framework of the present invention we prefer filling into ready-to-use sachets, which have the advantages of being easy to take orally, especially for children, and a unit distribution advantageous for children and for elderly people.

After taking up in solution, these compositions have no taste and have an appearance entirely acceptable to the consumer.

The present invention is illustrated by the following Examples.

EXAMPLE 1

The following compositions are used:

| | | | |
|---|---|---|---|
| trimipramine methanesulphonate: | 6.64 g | 3.38 g | 1.66 g |
| β-cyclodextrin | 50.00 g | 50.00 g | 50.00 g |
| water | 26.90 g | 26.71 g | 26.80 g |
| $\frac{\text{cyclodextrin}}{\text{trimipramine}}$ molar ratio | 2.6 | 5.2 | 10.4 |

The trimipramine methanesulphonate is dissolved in water and the cyclodextrin is wetted with the above solution. The whole is mixed with magnetic stirring for two hours at ambient temperature. The mixture is divided into 1.6 ml cells in an amount of 1.67 g (or about 100 mg of trimipramine) per dose and then lyophilized. Another experiment is carried out in which the paste is placed in a crystallizer and the whole is placed in a heated desiccator at 60° C. overnight.

After drying, either lyophilisates which are non-sticky to the touch are obtained in the first case or a perfectly fluid powder is obtained in the second case.

After dissolving in water (about 20 ml), a clear solution is obtained which is slightly bitter in the case of the example containing 100 mg of trimipramine base per dose, and tasteless in the case of the lower dosages. The solution is considerably less bitter than in the absence of cyclodextrin.

COMPARATIVE EXAMPLE 1

Example 1 is repeated using the first composition indicated but in the absence of cyclodextrin, that is to say trimipramine methanesulphonate (6.64 g) is placed in water (26.9 ml) and the solution obtained is dried. A mass is obtained in the form of gum which cannot be redissolved in water.

EXAMPLE 2

The following composition is used:

| | |
|---|---|
| trimipramine methanesulphonate | 0.44 g |
| β-cyclodextrin | 6.20 g |
| water | 2.50 g |
| isopropanol | 2.50 g |

The water and isopropanol are mixed and the cyclodextrin and then the trimipramine methanesulphonate are added. The mixture is stirred magnetically for one hour and a half. It is evaporated in a rotary evaporator for 40 minutes at 60° C. The powder obtained is redissolved; it has no taste whatever the concentration.

I claim:

1. A water soluble, solid pharmaceutical composition containing an inclusion compound, said pharmaceutical composition consisting essentially of β-cyclodextrin and imipramine or derivatives or salts thereof, said composition being prepared by forming an aqueous solution consisting essentially of β-cyclodextrin and imipramine or derivatives or salts thereof, drying the aqueous emulsion to form a non sticky pharmaceutical composition, wherein at least two moles of β-cyclodextrin are added per mole of imipramine or derivatives or salts thereof.

2. The inclusion compound of claim 1 wherein the aqueous solution comprises from 2 to 15 moles of βcyclodextrin per mole of imipramine or derivatives or salt.

3. A water soluble pharmaceutical composition consisting essentially of β-cyclodextrin and imipramine methane sulfonate, said composition being prepared by forming an aqueous solution of β-cyclodextrin and imipramine methane sulfonate, drying the aqueous solution to form a non-gummy composition.

4. The inclusion compound of claim 3 wherein the aqueous solution comprises from 2 to 15 moles of β-cyclodextrin per mole of imipramine or derivatives or salt.

* * * * *